(12) United States Patent
Bohner

(10) Patent No.: US 7,670,419 B2
(45) Date of Patent: Mar. 2, 2010

(54) HYDRAULIC CEMENT BASED ON CALCIUM PHOSPHATE FOR SURGICAL USE

(75) Inventor: Marc Bohner, Grenchen (CH)

(73) Assignee: Dr. H.C. Robert Mathys Stiftung, Bettlach (CH)

(*) Notice: Subject to any disclaimer, the term of this patent is extended or adjusted under 35 U.S.C. 154(b) by 776 days.

(21) Appl. No.: 10/598,500

(22) PCT Filed: Mar. 8, 2004

(86) PCT No.: PCT/CH2004/000134

§ 371 (c)(1), (2), (4) Date: Sep. 1, 2006

(87) PCT Pub. No.: WO2005/084726

PCT Pub. Date: Sep. 15, 2005

(65) Prior Publication Data

US 2007/0186818 A1 Aug. 16, 2007

(51) Int. Cl.
*C09K 3/00* (2006.01)

(52) U.S. Cl. .................... 106/35; 106/690; 106/691

(58) Field of Classification Search ............ 106/35, 106/690, 691
See application file for complete search history.

(56) References Cited

U.S. PATENT DOCUMENTS

| | | | |
|---|---|---|---|
| 5,782,971 A | 7/1998 | Constantz et al. | |
| 5,954,867 A * | 9/1999 | Chow et al. | 106/35 |
| 6,642,285 B1 * | 11/2003 | Bohner | 523/115 |
| 6,953,594 B2 * | 10/2005 | Lee et al. | 424/602 |
| 7,150,879 B1 * | 12/2006 | Lee et al. | 424/422 |
| 7,294,187 B2 * | 11/2007 | Chow et al. | 106/35 |
| 7,351,280 B2 * | 4/2008 | Khairoun et al. | 106/690 |
| 2003/0120351 A1 | 6/2003 | Tofighi et al. | |
| 2003/0199615 A1 | 10/2003 | Chaput et al. | |

FOREIGN PATENT DOCUMENTS

| | | |
|---|---|---|
| EP | 0 639 366 A1 | 2/1995 |
| WO | 2004000374 | 12/2003 |

OTHER PUBLICATIONS

U. Gbureck et al; "Mechanical activation and cement formation of beta-traicalcium phosphate"; Elsevier Science Publishers Publishers BV., Barking, GB; vol. 24, No. 23; Oct. 2003; pp. 4123-4131; XP004436346.

Siham Serraj et al.; "Effect on composition of dry mechanical grinding of calcium phosphate mixtures"; Journal of Biomedical Materials Research; vol. 55, No. 4; Jun. 15, 2001; pp. 566-575; XP002304973.

* cited by examiner

*Primary Examiner*—Paul Marcantoni
(74) *Attorney, Agent, or Firm*—Rankin, Hill & Clark LLP

(57) ABSTRACT

A hydraulic cement based on calcium phosphate for surgical use comprising A) a first component comprising powder particles of calcium phosphate; and B) a second component comprising water. The calcium phosphate comprises anhydrous, amorphous calcium phosphate (ACP) and the ACP is obtained by milling a calcium phosphate synthesized above 500° C. The cement according to the invention has the advantage of being very fast setting compared to prior art calcium phosphate cements. The setting reaction is finished much faster although the initial part of the reaction proceeds at the same speed as with known cements.

56 Claims, No Drawings

HYDRAULIC CEMENT BASED ON CALCIUM PHOSPHATE FOR SURGICAL USE

This invention concerns a hydraulic cement based on calcium phosphate for surgical use according to the preamble of claim 1.

Calcium phosphate cements (CPC) are mixtures of one or several calcium phosphate powders that react with water to form a new calcium phosphate compound, generally an apatite. Through these chemical reactions, there is hardening of the aqueous paste. In vivo studies have shown that CPC are generally biocompatible, osteoconductive and somehow bioresorbable. Therefore, CPC have been the subject of a large and growing interest of the medical community.

Several products have been introduced on the market. However, all of these products have some drawbacks. The main drawback is the slow setting reaction of apatite cements. The so-called setting time (time until which the paste is partially hard) might be short, e.g. 5-10 min, but the time until which the reaction is finished is typically longer than 24 hours. Several ways exist to control the setting time (see hereafter). However, until now, there are only two ways to accelerate the overall setting reaction. The first method is to decrease the average particle size of the starting components (e.g. a-tricalcium phosphate powder). In principle, the smaller the particle size, the faster the setting reaction. However, a decrease of the particle can be difficult to achieve (especially for diameters below 1 micrometer). The second method is to mill the powder until an amorphous phase is obtained ("Amorphous calcium phosphate, ACP"). The use of ACP for such cements has already been proposed, but the ACP has been obtained by wet milling of α-TCP, i.e. in a weight ratio of 1:1 for powder/liquid. Since the auxiliary liquid used in the milling process is an organic solvent there are considerable drawbacks for medical and commercial applications: (i) the cost of the milling procedure is increased; (ii) the ecological burden is higher; (iii) the solvent decomposes during milling, hence leading to organic residues which are difficult to remove; (iv) the wear weight fraction is increased—the risk of biocompatibility problems is strongly increased. A so-called ACP has been described in the literature in the past. However, this compound is obtained by precipitation in an aqueous solution, and typically contains bound water. In the present text, ACP is not obtained by precipitation, but by milling at high intensity and for a long time a calcium phosphate powder, e.g. alpha-tricalcium phosphate, beta-tricalcium phosphate, tetracalcium phosphate and oxyapatite.

The morphology of "milled ACP" is very different from that of "precipitated ACP" as observed by SEM. The latter compound has a well defined geometry (e.g. needles, plates), whereas the milled compound has a less-defined/undefined geometry (mostly round-shaped). Moreover, "milled ACP" has a well defined transition temperature at 400° C. (transformation into β-TCP) whereas "precipitated ACP" is transformed into α-TCP at 650° C.

It would be desirable therefore to provide a calcium phosphate cement which overcomes or alleviates in part or all of the above mentioned drawbacks. More specifically, the present invention describes compositions that harden faster than presently-known formulations, hence reducing the risks of mechanical failure in the first minutes and hours following cement implantation.

The invention solves the posed problem with a cement that displays the features of claim 1.

The cement according to the invention has the advantage of being very fast setting compared to prior art calcium phosphate cements. The setting reaction is finished much faster although the initial part of the reaction proceeds at the same speed as with known cements.

Preferably four calcium phosphate compounds can be used to produce an amorphous calcium phosphate (ACP) phase:

a) α-tricalcium phosphate [(α-TCP; $Ca_3(PO_4)_2$];

b) β-tricalcium phosphate [(β-TCP; $Ca_3(PO_4)_2$];

c) oxyapatite [(OXA); $Ca_{10}(PO_4)_6O$];

d) tetracalciumphosphate [TetCP; $Ca_4(PO_4)_2O$]

These four compounds can only be obtained at high temperature (at least 500° C.) and do not contain any hydroxyl groups (OH) like e.g. hydroxyapatite ($Ca_{10}(PO_4)_6(OH)_2$). As a result, ACP produced from milling these compounds is totally anhydrous.

Preferably the ACP is obtained by milling of one or more of the above four substances in the presence of not more than 20 weight percent of a non-aqueous auxiliary milling liquid compared to 100 weight percent of calcium phosphate. The auxiliary milling solvent can be an alcohol, preferably ethanol, or isopropanol which has the advantage of preventing agglomeration.

In a further embodiment said calcium phosphate contain— additionally to said ACP—one or several other calcium phosphates from the following list: monocalcium phosphate (MCP; $Ca(H_2PO_4)_2$); monocalcium phosphate monohydrate (MCPM; $Ca(H_2PO_4)_2.H_2O$), dicalcium phosphate (DCP; $CaHPO_4$), dicalcium phosphate dihydrate (DCPD; $CaHPO_4.2H_2O$); Octocalcium phosphate (OCP; $Ca_8H_2(PO_4)$ $6.5H_2O$); calcium deficient hydroxyapatite (CDHA; $Ca_9$ $(HPO_4)(PO_4)_5OH$), hydroxyapatite (HA; $Ca_{10}(PO_4)_6(OH)_2$), beta-tricalcium phosphate (b-TCP; Ca3(PO4)2), oxyapatite (OXA; $Ca_{10}(PO_4)_6O$), tetracalcium phosphate (TTCP; $Ca_4$ $(PO_4)_2O$), and a-tricalcium phosphate.

In a further embodiment the amorphous calcium phosphate (ACP) is present in an amount of at least 50 weight percent of the total first component, preferably in an amount of at least 80 weight percent and typically of at least 90 weight percent of the total first component.

In a further embodiment said first component comprises an amount of calcium sulfate dihydrate (CSD).

Still in a further embodiment the cement does not contain more calcium sulfate hemihydrate (CSH) than 10% of the total amount of said calcium sulfate dehydrate (CSD).

In another embodiment said first component comprises an amount of calcium sulfate hemihydrate (CSH). The amount of calcium sulfate hemihydrate (CSH) is preferably lower than 5% of said calcium sulfate dihydrate (CSD).

In a preferred embodiment essentially no calcium sulfate hemihydrate (CSH) is detectable in the cement.

In another embodiment the powder particles of said first component have an average diameter inferior to 20 μm and preferably inferior to 10 μm. Typically the average particle diameter is chosen to be 1 μm.

The setting time of the cement is an important property of the cement. If the setting time is too fast, the surgeon does not have time to use the cement before it is hard. If the setting time is too long, the surgeon must wait until he/she can close the wound. Therefore, an intermediate setting time is desirable. Values comprised between 1 and 20 minutes are in a good range. Preferable values are in the range of 2 to 15 minutes, in more details in the range of 5 to 12 minutes.

In a preferred embodiment at least one of the two cement components comprises a setting regulator; a setting regulator being either a setting accelerator or a setting retarder. A very efficient way to accelerate the setting time is to have large concentrations of phosphate and/or calcium ions in the mixing liquid (augmentation of the initial saturation of the solution towards apatite). This can happen via two ways: (i) a soluble phosphate and/or calcium salt is added as a powder in the cement formulation. Upon contact with the mixing solution, the phosphate and/or calcium salt dissolves, and hence accelerate the chemical reaction. (ii) a soluble phosphate and/or calcium salt is pre-dissolved in the mixing liquid. Examples of soluble phosphate salts are $Na_2HPO_4$, $NaH_2PO_4$, $K_2HPO_4$, $KH_2PO_4$, $NH_4H_2PO_4$, $CaCl_2$.

Typical concentrations in the mixing liquid are in the range of 0.01 to 1.00 M, preferentially in the range of 0.1 to 0.3 M. Another way to accelerate the setting reaction is to add nuclei for apatite crystal growth, as the nucleation step of the setting reaction is a limiting factor. Typically, apatite crystals can be used, preferably a calcium-deficient hydroxyapatite or hydroxyapatite powder. Small amounts (a few weight percents) are sufficient to drastically reduce the setting time.

When the setting time is too short, various setting additives can be added to increase the setting time. Typical examples are compounds which inhibits the nucleation and/or growth of apatite crystals. Common examples are pyrophosphate, citrate, or magnesium ions. One particularly interesting compound is calcium carbonate (CC; $CaCO_3$). Carbonate ions are present in human bone. Additionally, carbonate ions are able to reduce the size of apatite crystals, probably via the inhibition of apatite crystal growth.

The Ca/P molar ratio of a-TCP is 1.5. As a result, the Ca/P molar ratio of ACP obtained from milling a-TCP is also 1.5. Any change of this ratio after cement setting is expected to be associated with a change of solubility and hence of resorption rate. An easy way to modify this ratio is to add one or several calcium phosphates from the following list: monocalcium phosphate (MCP; $Ca(H_2PO_4)_2$; Ca/P=0.5); monocalcium phosphate monohydrate (MCPM; $Ca(H_2PO_4)2.H_2O$; Ca/P=0.5), dicalcium phosphate (DCP; $CaHPO_4$; Ca/P=1.0), dicalcium phosphate dihydrate (DCPD; $CaHPO_4.2H_2O$; Ca/P=1.0); Octocalcium phosphate (OCP; $Ca_8H_2(PO_4)6.5H_2O$; Ca/P=1.33); calcium deficient hydroxyapatite (CDHA; $Ca_9(HPO_4)(PO_4)_5OH$; Ca/P=1.50), alpha-tricalcium phosphate (a-TCP; $Ca_3(PO_4)_2$; Ca/P=1.50), beta-tricalcium phosphate (b-TCP; $Ca_3(PO_4)_2$; Ca/P=1.50), hydroxyapatite (HA; $Ca_{10}(PO_4)_6(OH)_2$; Ca/P=1.67), oxyapatite (OXA; $Ca_{10}(PO_4)_6O$), tetracalcium phosphate (TTCP; $Ca_4(PO_4)_2O$). Another way to modify this ratio is to add CSH or CSD. Simultaneously, an addition of CSH or CSD will allow an additional precipitation of apatite (during CSH or CSD in vivo dissolution), hence leading to large mechanical properties, and lower porosity. The apatite crystals are precipitated from the calcium ions released during the dissolution of CSH or CSD and the phosphate ions present in body fluids.

Similar combinations can be made with ACP obtained from milling b-TCP (Ca/P=1.5), OXA (oxyapatite; Ca/P=1.67) and TetCP (Ca/P=2.0).

In recent years, the occurrence of osteoporotic fractures has dramatically increased. Considering the lack of adequate cure and the increasing number of elderly people, this trend is expected to continue. Osteoporotic fractures are often very difficult to repair, because the bone is very weak. It is therefore not possible to insert screws to hold osteosynthesis plates. A way to solve the problem is to inject a calcium phosphate cement into the osteoporotic bone to reinforce it. In order to prevent any extravasation of the cement into the tissues surrounding bone, it is very important to visualize the cement. The easiest way is to increase the radio-opacity of the cement, for example by means of contrasting agents.

Metallic powders of Ta, Ti, or W (among others) can be used. Moreover, metal oxides or salts can be used, such as titanium dioxide or barium sulfate. However, it might not be desirable to use such powders in partially bioresorbable cements, particularly if the particles have a size smaller or equal to the size of foreign-body giant cell. It is preferable to use liquid agents, such as iodine compounds. Examples are iopamidol, iohexol and iotrolan.

The injection of a CPC into an osteoporotic bone is only possible if the cement is well injectable. Often, CPC are not well injectable. The reason is a too large average particle size and a too low viscosity of the mixing liquid, leading to so-called filter pressing: when a pressure is applied on the cement paste (e.g. during cement injection), the liquid and solid phases are separated. The easiest way to solve the problem is to increase the viscosity of the mixing liquid, for example by adding small amounts of polysaccharides into the mixing liquid. Typical polymers that can be used are hyaluronic acid or salt, chondroitin sulfate, dermantan sulfate, heparan sulfate, heparin, dextran, alginate, keratan sulfate, hydroxypropylmethyl cellulose, chitosan, xanthan gum, guar gum, carrageenan. The most interesting compounds are those already certified for medical applications, such as hyaluronate compounds. Typical concentrations are around 1% w/w.

The viscosity of the mixing liquid is (as seen above) important to prevent filter-pressing. The viscosity of the cement paste is also a very important factor. The cement viscosity should be high enough to prevent a too fast mix with body fluids, such as blood. A mix with body fluids could prevent cement setting and hence lead to complications. The paste viscosity is also very important to prevent cement extravasation during bone augmentation (injection of cement into bone): the larger the viscosity, the lower the risk of extravasation. Therefore, the cement viscosity should be larger than 1 Pa s, preferably above 10 or even 100 Pa s.

The viscosity of the cement paste depends obviously on the powder-to-liquid (P/L) ratio. An increase of the P/L ratio leads to a increase of the cement viscosity. If the P/L ratio is too high, the amount of mixing liquid is too low to fill up all the pores between the different solid particles, and hence to form a cement paste. The volume of mixing liquid (VL) should be in the range of: 0.5 VT<VL<10 VT where VT is the powder volume of the cement paste. More typical values are in the range of 1.0 VT<VL<2.5 VT. By volume is meant the real volume (and not the apparent volume), i.e. the weight divided by the density of the material.

CPC particles have the disadvantage that they do not have macropores, i.e. pores larger than 50-100 μm in diameter, in which blood vessels and bone cells can grow in.

As a result, the bioresorption occurs layer-by-layer and not everywhere in the cement bulk. To prevent this, bioresorbable or biodegradable granules can be added to the cement paste, in particular CSH and CSD granules. Upon implantation, CSH will first be transformed in CSD. Then, CSD granules produced from CSH transformation and CSD granules will dissolve, hence leaving empty pores. Typically, these granules, e.g. CSH or CSD granules, should have an average size in the range of 100 to 500 μm.

A different way to create macropores in the cement structure is to incorporate gas bubbles in the cement paste. This incorporation can be promoted by adding a tensioactive agent. Tensioactive agents can also be used to incorporate a poorly water-soluble contrasting agent into the cement paste, for example organic iodine compounds (see above). The tensio-active agent may be incorporated in one of said three components of the cement, preferably in the third component, and is preferably taken from the group of:

docusate sodium ($C_{20}H_{37}NaO_7S$), sodium lauryl sulfate ($C_{12}H_{25}NaO_4S$), stearic acid ($C_{17}H_{35}COOH$), alkyldimethyl (phenylmethyl)ammonium chloride [CAS registry number 8001-54-5], benzethonium chloride ($C_{27}H_{42}ClNO_2$), cetrimide ($C_{17}H_{38}BrN$), glycerin monooleate ($C_{21}H_{40}O_4$), polysorbate 20 ($C_{58}H_{114}O_{26}$), polysorbate 21 ($C_{26}H_{50}O_{10}$), polysorbate 40 ($C_{62}H_{122}O_{26}$), polysorbate 60 ($C_{64}H_{126}O_{26}$), polysorbate 61 ($C_{32}H_{62}O_{10}$), polysorbate 65 ($C_{100}H_{194}O_{28}$), polysorbate 80 ($C_{64}H_{124}O_{26}$), polysorbate 81 ($C_{34}H_{64}O_{11}$), polysorbate 85 ($C_{100}H_{188}O_{28}$), polysorbate 120 ($C_{64}H_{126}O_{26}$), polyvinyl alcohol (($C_2H_4O)_n$), sorbitan di-isostearate ($C_{42}H_{80}O_7$), sorbitan dioleate ($C_{42}H_{76}O_7$), sorbitan monoisostearate ($C_{24}H_{46}O_6$), sorbitan monolaurate ($C_{18}H_{34}O_6$), sorbitan monooleate ($C_{24}H_{44}O_6$), sorbitan monopalmitate ($C_{22}H_{42}O_6$), sorbitan monostearate ($C_{24}H_{46}O_6$), sorbitan sesqui-isostearate ($C_{33}H_{63}O_{6.5}$), sorbitan sesquioleate ($C_{33}H_{63}O_{6.5}$), sorbitan sesquistearate ($C_{33}H_{63}O_{6.5}$), sorbitan tri-isostearate ($C_{33}H_{63}O_{6.5}$), sorbitan trioleate ($C_{33}H_{63}O_{6.5}$), sorbitan tristearate ($C_{33}H_{63}O_{6.5}$), glyceryl monooleate ($C_{21}H_{40}O_4$), isopropyl myristate ($C_{17}H_{34}O_2$), isopropyl palmitate ($C_{19}H_{38}O_2$), lanolin [CAS registry number 8006-54-0], lanolin alcohols [CAS registry number 8027-33-6], hydrous lanolin [CAS registry number 8020-84-6], lecithin [CAS registry number 8002-43-5], medium chain triglycerides (no registry number), monoethanolamine ($C_2H_7NO$), oleic acid ($C_{17}H_{33}COOH$), polyethylene glycol monocetyl ether [CAS registry number 9004-95-9], polyethylene glycol monostearyl ether [CAS registry number 9005-00-9], polyethylene glycol monolauryl ether [CAS registry number 9002-92-0], polyethylene glycol monooleyl ether [CAS registry number 9004-98-2], polyethoxylated castor oil [CAS registry number 61791-12-6], polyoxyl 40 stearate ($C_{98}H_{196}O_{42}$), polyoxyl 50 stearate ($C_{118}H_{236}O_{52}$), triethanolamine ($C_6H_{15}NO_3$), anionic emulsifying wax [CAS registry number 8014-38-8], nonionic emulsifying wax [CAS registry number 977069-99-0], and sodium dodecyl sulfate ($NaC_{12}H_{25}SO_4$).

Quite often, bone defects are not due to a traumatic event, but to a disease, e.g. bone tumor or infection. In these cases, it would be interesting to incorporate drugs, in particular pharmaceutically or physiologically active substances, preferably antibiotics, anti-inflammatory drugs, anti-cancer drugs, peptides, and proteins such as growth factors.

The various features of novelty which characterize the invention are pointed out with particularity in the claims annexed to and forming part of this disclosure. For the better understanding of the invention, its operating advantages and specific objects attained by its use, reference should be made to the examples and descriptive matter in which are illustrated and described preferred embodiments of the invention.

EXAMPLE 1

α-TCP powder was dry-milled for 4 hours in a planetary mill at 400 RPM ($ZrO_2$ beads, $ZrO_2$ containers). The resulting ACP powder was 87% pure according to XRD (Rietveld refinement analysis), the rest being α-TCP. 0.001% $ZrO_2$ was found in the resulting ACP powder using x-ray fluoroscopy (XRF). To produce the cement, 10 g of the ACP powder were mixed for 30 seconds with 3.5 mL of $Na_2HPO_4$ 0.15M (using a beaker and a spatula). The resulting paste had a setting time of 5.6+/−0.9 min (95% interval of confidence on the mean) at room temperature (22+/−2 C). The cement was incubated in a phosphate buffer solution (pH 7.4) for 1, 3, 6 and 24 hours at 37 C and tested mechanically. No significant difference of the wet compressive strength was found between the various aging conditions. The average value was: 21+/−3 MPa (95% interval of confidence on the mean; average of the results obtained at 1, 3, 6 and 24 hours). The samples were then dried and analyzed by XRD. None of the samples contained α-TCP or ACP residues.

EXAMPLE 2

β-TCP powder was milled with 5 w % isopropanol (100 g powder, 5 g ethanol) for 6 hours in a planetary mill at 400 RPM ($ZrO_2$ beads, $ZrO_2$ containers). The resulting ACP powder was dried at 100 C for 3 hours. The resulting powder was 82% pure according to XRD (Rietveld refinement analysis), the rest being β-TCP. 0.003% $ZrO_2$ was found in the resulting ACP powder (XRF). To produce the cement, 10 g of the ACP powder and 0.2 g MCPM were mixed for 30 seconds with 3.5 mL of $Na_2HPO_4$ 0.15M (using a beaker and a spatula). The resulting paste had a setting time of 7.8+/−1.2 min (95% interval of confidence on the mean) at room temperature (22+/−2 C). The cement was incubated in a phosphate buffer solution (pH 7.4) for 1, 3, 6 and 24 hours at 37 C and tested mechanically. The compressive strength was significantly lower after 1 hour compared to 3, 6 and 24 hours. The average value was: 15+/−5 MPa after 1 hour and 25+/−3 MPa afterwards (95% interval of confidence on the mean; average of the results obtained at 3, 6 and 24 hours). The samples were then dried and analyzed by XRD. All samples contained β-TCP residues. The samples incubated for one hour contained some ACP residues (Rietveld refinement analysis).

EXAMPLE 3

α-TCP powder was dry-milled for 4 hours in a planetary mill at 400 RPM ($ZrO_2$ beads, $ZrO_2$ containers). The resulting ACP powder was 87% pure according to XRD (Rietveld refinement analysis), the rest being α-TCP. 0.001% $ZrO_2$ was found in the resulting ACP powder (XRF). To produce the cement, 10 g of the ACP powder and 0.4 g $K_2HPO_4$ powder were mixed for 30 seconds with 4.0 mL of a 1 w % sodium hyaluronate solution (using a beaker and a spatula). The resulting paste had a setting time of 11.1+/−1.5 min (95% interval of confidence on the mean) at room temperature (22+/−2 C). The cement samples were incubated in a phosphate buffer solution (pH 7.4) for 24 hours at 37 C and tested mechanically. The compressive strength was 17+/−4 MPa (95% interval of confidence on the mean). The samples were then dried and analyzed by XRD. The samples appeared to consist of 100% calcium-deficient hydroxyapatite. Some of the cement pastes were injected with a syringe and cannula into a phosphate buffer solution (pH 7.4) at 37 C, either 2, 3, 4 or 6 minutes after the start of mixing. None of the pastes decomposed during setting. Hard blocks were obtained.

EXAMPLE 4

α-TCP powder was dry-milled for 4 hours in a planetary mill at 400 RPM ($ZrO_2$ beads, Z $ZrO_2$ containers). The initial and final SSA values were 0.6+/−0.1 and 2.7+/−0.3 m2/g, respectively. The resulting ACP powder was 87% pure according to XRD (Rietveld refinement analysis). The rest consisted in α-TCP. 0.001% ZrO2 was found in the resulting ACP powder (XRF). To produce the cement, 10 g of the ACP powder and 0.4 g $K_2HPO_4$ powder were mixed for 30 seconds with 2.0 mL of a 2 w % sodium hyaluronate solution and 2.0 mL of a iodine compound (Ultravist 300) (using a beaker and a spatula). The resulting paste had a setting time of 8.1+/−1.3 min (95% interval of confidence on the mean) at room temperature (22+/−2 C). The cement samples were incubated in a phosphate buffer solution (pH 7.4) for 24 hours at 37 C and tested mechanically. The compressive strength was 18+/−4 MPa (95% interval of confidence on the mean). The samples were then dried and analyzed by XRD. The samples appeared to consist of 100% calcium-deficient hydroxyapatite.

EXAMPLE 5

β-TCP was dry-milled separately for 6 hours in a planetary mill at 400 RPM ($ZrO_2$ beads, $ZrO_2$ containers). The resulting ACP powder was 82 pure according to XRD (Rietveld refinement analysis), the rest being β-TCP. 0.003% $ZrO_2$ were found in the resulting ACP powder (XRF). To produce the cement, 6.3 g of the ACP powder obtained from b-TCP milling and 3.7 g of TTCP were mixed for 30 seconds with 1.0 mL of a 3 w % sodium hyaluronate gel and 4.0 mL of a iodine compound (Ultravist 300) (using a beaker and a spatula). The resulting paste had a setting time of 10.1+/−2.0 min (95% interval of confidence on the mean) at room temperature (22+/−2 C). The cement samples were incubated in a phosphate buffer solution (pH 7.4) for 24 hours at 37 C and tested mechanically. The compressive strength was 12+/−3 MPa (95% interval of confidence on the mean). The samples were then dried and analyzed by XRD. The samples consisted of 100% hydroxyapatite.

EXAMPLE 6

Oxyapatite powder was milled with 2 w % ethanol (2 g ethanol for 100 g HA) for 12 hours in a planetary mill at 400 RPM ($ZrO_2$ beads, $ZrO_2$ containers). The resulting ACP powder had a SSA of 3.3 $m^2$/g and was 93% pure according to XRD (Rietveld refinement analysis), the rest being HA. 0.014% $ZrO_2$ was found in the resulting ACP powder (XRF). To produce the cement, 45 g of the ACP powder and 5 g of CDHA powder were stirred vigorously (at 2000 RPM with a stirring bar) with 30 mL of a 0.01 w % polyethoxylate castor oil solution until an emulsion (air in cement) was obtained. The resulting paste was poured into a mold. After 20 min at room temperature (22+/−2 C), 10 mL of a phosphate buffer solution (pH 7.4) was poured on top of the cement-air mixture, and the mould was covered with a lid. The paste was incubated for 24 hours at 37 C. After 24 hours, the samples were unmoulded and dried in air until constant weight was reached. The porosity of the resulting block was 88 vol.-%. The average macropore diameter (as estimated from optical microscopy) was 230 micrometers. The compressive strength was low, i.e. 1.6+/−0.3 MPa (95% interval of confidence on the mean). The samples were then dried and analyzed by XRD. No significant ACP residues could be identified (Rietveld refinement analysis).

EXAMPLE 7

TetCP powder was dry-milled for 3 hours in a planetary mill at 400 RPM ($ZrO_2$ beads, $ZrO_2$ containers). The resulting ACP powder was 73% pure according to XRD (Rietveld refinement analysis), the rest being TetCP. 0.004% $ZrO_2$ was found in the resulting ACP powder using x-ray fluoroscopy (XRF). To produce the cement, 10 g of the ACP powder and 3.72 g of dicalcium phosphate (CaHPO4) were mixed for 30 seconds with 4.5 mL of $Na_2HPO_4$ 0.05M (using a beaker and a spatula). The resulting paste had a setting time of 11.3+/−2.1 min (95% interval of confidence on the mean) at room temperature (22+/−2 C). The cement was incubated in a phosphate buffer solution (pH 7.4) for 1, 3, 6 and 24 hours at 37 C and tested mechanically. No significant difference of the wet compressive strength was found between the various aging conditions. The average value was: 33+/−3 MPa (95% interval of confidence on the mean; average of the results obtained at 1,3, 6 and 24 hours). The samples were then dried and analyzed by XRD. The samples consisted of pure hydroxyapatite. None of the samples obtained at and beyond 3 hours contained detectable amounts of TetCP or ACP residues. Small amounts of TetCP were detected at 1 and hours.

The invention claimed is:

1. A hydraulic cement based on calcium phosphate for surgical use comprising:
    A) a first component comprising powder particles of calcium phosphate; and
    B) a second component comprising water, wherein:
    C) said calcium phosphate comprises anhydrous, amorphous calcium phosphate (ACP);
    D) said ACP is obtained by milling a calcium phosphate synthesized above 500° C.;
    E) said ACP is able to react with water thereby producing a cement paste that becomes a hardened cement;
    F) the specific surface area (SSA) of the powder particles of said first component is in the range of 0.05 to 10.00 $m^2$/g; and
    G) said first component further comprises calcium sulfate dihydrate (CSD) or calcium sulfate hemihydrate (CSH).

2. A hydraulic cement according to claim 1, wherein said ACP is obtained by milling of one or more substances chosen from the group consisting of:
    a) α-tricalcium phosphate [(α-TOP; $Ca_3(PO_4)_2$)];
    b) β-tricalcium phosphate [(β-TCP; $Ca_3(PO_4)_2$)];
    c) oxyapatite [(OXA); $Ca_{10}(PO_4)_6O$]; and
    d) tetracalciumphosphate [TetCP; $Ca_4(PO_4)_2O$];
in the presence of not more than 20 weight percent of a non-aqueous auxiliary milling liquid compared to 100 weight percent of calcium phosphate.

3. A hydraulic cement according to claim 2, wherein the auxiliary milling solvent is an alcohol.

4. A hydraulic cement according to claim 1, wherein in addition to said ACP, said cement contains one or several other calcium phosphates selected from the group consisting of: monocalcium phosphate (MCP; $Ca(H_2PO_4)_2$); monocalcium phosphate monohydrate (MCPM; $Ca(H_2PO_4)_2H_2O$), dicalcium phosphate (DCP; $CaHPO_4$), dicalcium phosphate dihydrate (DCPD; $CaHPO_4 2H_2O$); octacalcium phosphate (OCP; $Ca_8H_2(PO_4)_6.5H_2O$); calcium deficient hydroxyapatite (CDHA; $Ca_9(HPO_4)(PO_4)_5OH$), hydroxyapatite (HA; $Ca_{10}(PO_4)_6(OH)_2$), beta-tricalcium phosphate (β-CP; $Ca_3(PO_4)_2$), oxyapatite (OXA; $Ca_{10}(PO_4)_6O$), tetracalcium phosphate [TTCP; $Ca_4(PO_4)_2O$] and α-tricalcium phosphate.

5. A hydraulic cement according to claim 1, wherein the amorphous calcium phosphate (ACP) is present in an amount of at least 50 weight percent of the total first component.

6. A hydraulic cement according to claim 5, wherein the amorphous calcium phosphate (ACP) is present in an amount of at least 80 weight percent of the total first component.

7. A hydraulic cement according to claim 1, wherein said first component comprises calcium sulfate dihydrate (CSD).

8. A hydraulic cement according to claim 7, wherein said hydraulic cement does not contain more calcium sulfate hemihydrate (CSH) than 10% of the total amount of said calcium sulfate dihydrate (CSD).

9. A hydraulic cement according to claim 1 wherein said first component comprises calcium sulfate hemihydrate (CSH).

10. A hydraulic cement according to claim 9, wherein the amount of calcium sulfate hemihydrate (CSH) is lower than 5% of said calcium sulfate dihydrate (CSD).

11. A hydraulic cement according to claim 7, wherein essentially no calcium sulfate hemihydrate (CSH) is detectable in the cement.

12. A hydraulic cement according to claim 1, wherein the powder particles of said first component have an average diameter less than 20 µm.

13. A hydraulic cement according to claim 1, wherein at least one of the first and second cement components comprises a setting regulator.

14. A hydraulic cement according to claim 1, wherein at least one of the first and second cement components comprises a setting accelerator.

15. A hydraulic cement according to claim 14, wherein the first component comprises a setting accelerator.

16. A hydraulic cement according to claim 14, wherein the setting accelerator is an apatite powder.

17. A hydraulic cement according to claim 14, wherein the setting accelerator is a calcium-deficient hydroxyapatite or hydroxyapatite powder.

18. A hydraulic cement according to claim 14, wherein the setting accelerator is a water-soluble calcium salt.

19. A hydraulic cement according to claim 1, wherein the second component comprises a setting accelerator.

20. A hydraulic cement according to claim 19, wherein the setting accelerator is a dissolved calcium salt.

21. A hydraulic cement according to claim 13, wherein the setting regulator is a setting retarder.

22. A hydraulic cement according to claim 1, wherein the first or second component comprises a setting retarder.

23. A hydraulic cement according to claim 21, wherein the setting retarder is selected from the group consisting of citrate, pyrophosphate, carbonate and magnesium ions.

24. A hydraulic cement according to claim 1, wherein the setting time of the cement paste at is comprised between 2 and 15 minutes.

25. A hydraulic cement according to claim 24, wherein the setting time of the cement paste at 37° C. is between 5 and 12 minutes.

26. A hydraulic cement according to claim 1, wherein the Ca/P molar ratio of the cement paste obtained by mixing said components is larger than 1.5.

27. A hydraulic cement according to claim 26, wherein the Ca/P molar ratio of the cement paste is equal to 1.667.

28. A hydraulic cement according to claim 26, wherein the Ca/P molar ratio of the cement paste is larger than 1.667.

29. A hydraulic cement according to claim 26, wherein the Ca/P molar ratio of the cement paste is equal or larger than 2.0.

30. A hydraulic cement according to claim 1, wherein at least one of the first and second components contains a radiological contrasting agent.

31. A hydraulic cement according to claim 30, wherein the radiological contrasting agent is a solid compound.

32. A hydraulic cement according to claim 31, wherein said solid radiological contrasting agent is present in particle form whereby said particles have a diameter larger than 10 micrometer.

33. A hydraulic cement according to claim 31, wherein the radiological contrasting agent is a metal powder.

34. A hydraulic cement according to claim 31, wherein the radiological contrasting agent is a ceramic powder.

35. A hydraulic cement according to claim 30, wherein the radiological contrasting agent is a liquid compound.

36. A hydraulic cement according to claim 35, wherein the radiological contrasting agent is an organic iodine compound.

37. A hydraulic cement according to claim 1, wherein one of said two components comprises an additive to control the cement rheology.

38. A hydraulic cement according to claim 37, wherein the second component comprises an additive to control the cement rheology.

39. A hydraulic cement according to claim 37, wherein the additive used to control the cement rheology is selected from the group consisting of hyaluronic acid or salt, chondroitin sulfate, dermantan sulfate, heparan sulfate, heparin, dextran, alginate, keratan sulfate, hydroxypropylmethyl cellulose, chitosan, xanthan gum, guar gum, and carrageenan.

40. A hydraulic cement according to claim 37, wherein the additive used to control the cement rheology is acid and/or one of its salts.

41. A hydraulic cement according to claim 1, wherein the first or second component of the cement may further comprise granules whose diameter are at least two times larger than the average diameter of said powder particles of said first component.

42. A hydraulic cement according to claim 41, wherein the granules have an average diameter in the range of 100 to 500 µm.

43. A hydraulic cement according to claim 41, wherein the granules are made of calcium phosphate, calcium sulfate hemihydrate, calcium sulfate dihydrate, polymer, sodium chloride, bioglass or a sugar.

44. A hydraulic cement according to claim 1, wherein one or more of said components comprises pharmaceutical or physiologically active substances.

45. A hydraulic cement according to claim 1, wherein one of said components comprises a tensio-active agent selected from the group consisting of: docusate sodium ($C_{20}H_{37}NaO_7S$), sodium lauryl sulfate ($C_{12}H_{25}NaO_4S$), stearic acid ($C_{17}H_{35}COOH$), alkyldimethyl(phenylmethyl)-ammonium chloride [CAS registry number 8001-54-5], benzethonium chloride ($C_{27}H_{42}ClNO_2$), cetrimide ($C_{17}H_{38}BrN$), glycerin monooleate ($C_{21}H_{40}O_4$), polysorbate 20 ($C_{58}H_{114}O_{26}$), polysorbate 21 ($C_{26}H_{50}O_{10}$), polysorbate 40 ($C_{62}H_{122}O_{26}$), polysorbate 60 ($C_{64}H_{126}O_{26}$), polysorbate 61 ($C_{32}H_{62}O_{10}$), polysorbate 65 ($C_{100}H_{194}O_{28}$), polysorbate 80 ($C_{64}H_{124}O_{26}$), polysorbate 81 ($C_{34}H_{64}O_{11}$), polysorbate 85 ($C_{100}H_{188}O_{28}$), polysorbate 120 ($C_{64}H_{126}O_{26}$), polyvinyl alcohol ($((C_2H_4O)_n)$), sorbitan di-isostearate ($C_{24}H_{80}O_7$), sorbitan dioleate ($C_{42}H_{76}O_4$, sorbitan monoisostearate ($C_{24}H_{46}O_6$), sorbitan monolaurate ($C_{18}H_{34}O_6$), sorbitan monooleate ($C_{24}H_{44}O_6$) sorbitan monopalmitate ($C_{22}H_{42}O_6$), sorbitan monostearate ($C_{24}H_{46}O_6$), sorbitan sesqui-isostearate ($C_{33}H_{63}O_{6.5}$), sorbitan sorbitan sesquistearate (C33H63O6.5), sorbitan tri-isostearate ($C_{33}H_{63}O_{6.5}$), sorbitan sesquioleate ($C_{33}H_{63}O_{6.5}$), sorbitan sesquistearate ($C_{33}H_{63}O_{6.5}$), sorbitan tri-isostearate ($C_{33}H_{63}O_{6.5}$), sorbitan trioleate ($C_{33}H_{63}O_{6.5}$), sorbitan tristearate ($C_{33}H_{63}O_{6.5}$), glyceryl monooleate ($C_{21}H_{40}O_4$), isopropyl myristate ($C_{17}H_{34}O_2$), isopropyl palmitate ($C_{19}H_{36}O_2$), lanolin [CAS registry number 8006-54-0], lanolin alcohols [CAS registry number 8027-33-6], hydrous lanolin [CAS registry number 8020-84-6], lecithin [CAS registry number 8002-43-5], medium chain triglycerides (no registry number), monoethanolamine ($C_2H_7NO$), oleic acid ($C_{17}H_{33}COOH$), polyethylene glycol monocetyl ether [CAS registry number 9004-95-9], polyethylene glycol monostearyl ether [CAS registry number 9005-00-9], polyethylene glycol monolauryl ether [CAS registry number 9002-92-0], polyethylene monooleyl ether [CAS registry number 9004-98-2], polyethoxylated castor oil [CAS registry number 61791-12-6], polyoxyl 40 stearate ($C_{98}H_{196}O_{42}$), polyoxyl 50 stearate ($C_{118}H_{236}O_{52}$), triethanolamine ($C_6H_{15}NO_3$), anionic emulsifying wax [CAS registry number 8014-38-8], nonionic emulsifying wax [CAS registry number 977069-99-0], and sodium dodecyl sulfate ($NaC_{12}H_{25}SO_4$).

46. A hydraulic cement according to claim 1, wherein the specific surface area (SSA) of the first component is in the range of 1.5 to 3.5 $m^2/g$.

47. A hydraulic cement according to claim 1, wherein the cement viscosity of the cement is larger than 1 Pa-s at a shear rate of 400 $s^{-1}$, one minute after the start of cement mixing.

48. A hydraulic cement according to claim 47, wherein the cement viscosity of the cement is larger than 10 Pa-s at a shear rate of 400 $s^{-1}$, one minute after the start of cement mixing.

49. A hydraulic cement according to claim 48, wherein the cement viscosity of the cement is larger than 100 Pa-s at a shear rate of 400 $s^{-1}$, one minute after the start of cement mixing.

50. A hydraulic cement according to claim 49, wherein component "a)" additionally comprises water-soluble phosphate salts and component "b)" comprises a polymer.

51. A hydraulic cement according to claim 1, wherein the setting time of the mixture of said two components is between 2 to 15 minutes.

52. A method of using the cement according to claim 1, wherein the mixture of said two components is injected into an animal or human bone defect and set in vivo to reinforce the bone.

53. A method for producing a matrix of apatite as temporary bone replacement material, wherein said two components according to claim 1 are mixed together and allowed to harden.

54. A temporary bone replacement material obtained by the method according to claim 53, wherein the replacement material comprises an apatite.

55. The temporary bone replacement material according to claim 54, wherein the replacement material comprises CSD embedded in said apatite matrix.

56. A granule or block obtained by hardening the cement according to claim 1 for in vivo implants.

* * * * *